United States Patent
Landi et al.

(10) Patent No.: US 11,701,070 B2
(45) Date of Patent: Jul. 18, 2023

(54) MEDICAL OR DENTAL IMAGING SYSTEM WITH MOTION COMPENSATION

(71) Applicant: See Through S.r.l., Brusaporto (IT)

(72) Inventors: Claudio Landi, Milan (IT); Cristina Sarti, Frankfurt am Main (DE); Michael Reiter, Elsbethen (AT)

(73) Assignee: See Through S.r.l., Brusaporto (IT)

(*) Notice: Subject to any disclaimer, the term of this patent is extended or adjusted under 35 U.S.C. 154(b) by 64 days.

(21) Appl. No.: 17/242,949

(22) Filed: Apr. 28, 2021

(65) Prior Publication Data
US 2021/0330276 A1    Oct. 28, 2021

(30) Foreign Application Priority Data
Apr. 28, 2020    (EP) .................................... 20171850

(51) Int. Cl.
| | |
|---|---|
| *A61B 6/14* | (2006.01) |
| *A61B 6/04* | (2006.01) |
| *A61B 6/00* | (2006.01) |
| *A61B 6/03* | (2006.01) |

(52) U.S. Cl.
CPC ............. *A61B 6/14* (2013.01); *A61B 6/0492* (2013.01); *A61B 6/501* (2013.01); *A61B 6/527* (2013.01); *A61B 6/547* (2013.01); *A61B 6/032* (2013.01); *A61B 6/4435* (2013.01)

(58) Field of Classification Search
None
See application file for complete search history.

(56) References Cited

U.S. PATENT DOCUMENTS

| | | | | |
|---|---|---|---|---|
| 8,885,177 B2* | 11/2014 | Ben-Yishai | .......... | G01B 11/002 356/614 |
| 9,138,319 B2* | 9/2015 | Fanson | ................ | A61B 34/20 |
| 10,052,079 B2* | 8/2018 | Abkai | .................... | A61B 6/547 |
| 10,117,748 B2* | 11/2018 | Fanson | ................ | A61B 90/39 |
| 10,223,798 B2* | 3/2019 | Hladio | .................. | A61B 34/20 |
| 10,424,115 B2* | 9/2019 | Ellerbrock | ............... | H04N 5/32 |
| 10,438,359 B2* | 10/2019 | Hladio | .................. | A61B 34/20 |
| 10,650,536 B2* | 5/2020 | Hladio | .................. | G06T 7/246 |
| 11,229,520 B2* | 1/2022 | Fanson | ................ | A61B 34/25 |

(Continued)

FOREIGN PATENT DOCUMENTS

EP    2937058    10/2015

OTHER PUBLICATIONS

European Search Report for European Application No. 20171850.9, dated Oct. 8, 2020.

*Primary Examiner* — Thomas R Artman
(74) *Attorney, Agent, or Firm* — Klarquist Sparkman, LLP

(57) ABSTRACT

A medical or dental imaging system for generating an image of a part of the head, comprising: an x-ray source and an x-ray detector which move around the head to generate x-ray images at different positions, a tracking device which provides sensor data indicative of any movement of the head during the acquisition of the x-ray images and a computer which generates tracking data based on the sensor data and calculates an x-ray image of the head part based on the x-ray images and on the tracking data to compensate for any movement of the head part during the acquisition of the x-ray images, wherein the tracking device comprises at least one camera and an attachment device for detachable attachment of the camera to the patient.

20 Claims, 2 Drawing Sheets

(56) References Cited

U.S. PATENT DOCUMENTS

| | | | |
|---|---|---|---|
| 11,321,849 B2* | 5/2022 | Hladio | A61B 34/20 |
| 2009/0220122 A1* | 9/2009 | Richards | A61B 34/20 |
| | | | 382/128 |
| 2010/0066802 A1* | 3/2010 | Dross | H04N 7/185 |
| | | | 348/14.02 |
| 2012/0157887 A1* | 6/2012 | Fanson | A61F 2/46 |
| | | | 600/595 |
| 2013/0190887 A1* | 7/2013 | Fanson | A61F 2/46 |
| | | | 623/22.12 |
| 2014/0078517 A1* | 3/2014 | Ben-Yishai | G01B 11/002 |
| | | | 356/614 |
| 2015/0310668 A1* | 10/2015 | Ellerbrock | A61C 1/084 |
| | | | 345/633 |
| 2015/0313684 A1* | 11/2015 | Fanson | A61F 2/46 |
| | | | 600/424 |
| 2016/0166226 A1 | 6/2016 | Abkai et al. | |
| 2017/0345177 A1* | 11/2017 | Hladio | G06T 7/246 |
| 2019/0070011 A1* | 3/2019 | Fanson | A61F 2/32 |
| 2019/0156493 A1* | 5/2019 | Hladio | G06T 7/246 |
| 2020/0043178 A1* | 2/2020 | Hladio | G06T 7/246 |
| 2020/0273178 A1* | 8/2020 | Hladio | G06T 7/246 |
| 2021/0330276 A1* | 10/2021 | Landi | A61B 6/527 |
| 2022/0175537 A1* | 6/2022 | Fanson | A61B 34/25 |

* cited by examiner

MEDICAL OR DENTAL IMAGING SYSTEM WITH MOTION COMPENSATION

CROSS REFERENCE TO RELATED APPLICATION

The present application claims priority from pending European Patent Application No. EP 20171850.9, filed Apr. 28, 2020, which is incorporated herein by reference.

FIELD

The present application relates to a medical or dental imaging system for generating an image of at least a part of the head of a patient which is configured to compensate for any movement of the head part during the acquisition of the image in order to avoid or reduce blur of the images of the head part.

DESCRIPTION OF PRIOR ART

Such a medical or dental imaging system is known for example from patent application US 2016/0166226 A1. A camera is mounted on an element of the medical or dental imaging system, e.g., on an x-ray source or on an x-ray detector or on a carrying arm, and thus has a defined position relative to the medical or dental imaging system. The camera is configured to record images of optical marks which are fixed to the head of the patient. Thus, the exact positional relationship between the marks on the patient's head and the element of the medical or dental imaging system carrying the camera can be determined. When calculating a three-dimensional x-ray image of the head part, a computer uses these images of the camera and the determined positional relationship to compensate for any movement of the head part during the acquisition of the x-ray images, and thus avoids blurred three-dimensional x-ray images.

SUMMARY

It is therefore an object to improve this known technology and to provide in particular a medical or dental imaging system having a more robust and accurate determination of the patient motion.

According to an embodiment a medical or dental imaging system for generating an image of at least one part of the head of a patient comprises a frame or supporting structure, a rotation unit having an x-ray source and an x-ray detector, a tracking device which is configured to provide sensor data indicative of any movement of the at least one part of the head and a computer configured to calculate a three-dimensional x-ray image of the at least one head part.

The patient may preferably be a human being or an animal. The at least one part of the head of the patient to be imaged by the medical or dental imaging system may comprise for example a forehead, a face, an oral cavity, a jaw, at least one tooth, a dental root canal, a nasal bone, or any other part of the head of the patient.

The frame or supporting structure is preferably a carrier for various components of the medical or dental imaging system, in particular for the rotation unit. Especially preferable, the frame or supporting structure comprises at least one of a column, a base or floor stand and a fixed arm.

The x-ray source of the rotation unit is configured for the emission of x-rays towards at least one part of the head of a patient. The x-ray source preferably comprises a cone-beam or fan-beam x-ray source. The x-ray detector is configured to receive at least a portion of the x-rays emitted by the x-ray source, in particular x-rays which are emitted toward the at least one part of the head to be imaged and/or which pass through the at least one part of the head to be imaged. Based on these received x-rays the medical or dental imaging system, in particular the computer, is configured to generate an image of the at least one part of the head. The x-ray source and the x-ray detector are at least parts of the rotation unit.

The rotation unit with the x-ray source and the x-ray detector is rotatably coupled to the frame, in particular the fixed arm of the frame, and is configured to move around the head or head part (to be imaged) so that the x-ray source and the x-ray detector take up a plurality of different positions to generate a plurality of x-ray images at said different positions. Preferably, the rotation unit is rotatably coupled to the frame or fixed arm at a pivot point, in particular at a free end of the fixed arm. The pivot point and/or the rotation unit preferably comprise(s) a rotational axis around which the rotation unit with the x-ray source and the x-ray detector rotate. The pivot point preferably comprises a pivot bearing.

The rotation unit preferably comprises a rotating arm or cantilever, in particular a rotating arm having a C-shape. The x-ray source and the x-ray detector are preferably arranged on opposite end sections or (free) ends of the rotating arm such that they face one another.

The tracking device is configured to provide sensor data indicative of any movement of the at least one part of the head during the acquisition of the plurality of x-ray images of the at least one part of the head. The tracking device is preferably configured to transmit the sensor data to the computer to generate tracking data based on the sensor data.

The tracking device comprises at least one camera which is configured to face and record at least one tracking marker of the tracking device in order to generate the sensor data. The sensor data provided by the camera preferably comprise optical sensor data. The optical sensor data comprise images of the at least one tracking marker. The sensor data are indicative of any movement of the head or at least one part of the head in particular due to different (spatial) positions of the markers on images taken at different moments. The different spatial positions of the markers may for example be caused by a horizontal and/or vertical movement of the head or at least one head part to be imaged, in particular by a tilting and/or nodding motion and/or rotation around the vertical axis of the head or head part.

The tracking data based on or derived from the sensor data, in particular the images of the at least one tracking marker, and generated by the computer may comprise for example a plurality of positions or a trajectory of the at least one tracking marker, in particular a trajectory of the head or the at least one part of the head, in particular relative to the at least one tracking marker and/or at least a component of the medical or dental imaging system, for example at least one of the x-ray source, the x-ray detector, the rotating arm of the rotation unit or the column. The tracking data are in particular provided for recording the movement of the at least one part of the head while the plurality of x-ray images is taken and for compensation of the movement of the head or at least one part of the head which is imaged.

The medical or dental imaging system preferably comprises a chinrest or headrest for the patient which is configured to support the head, in particular the at least one part of the head which is to be imaged, or the chin. Due to the support of the head on the chinrest the movement to be tracked by the tracking device particularly comprises tilting or nodding movements of the head or at least one part of the head, rather than linear or lateral movements. Such tilting or nodding movements are easier to distinguish from lateral or linear movements and easier to measure by a tracking device having an attachment device for detachable attachment of at least one camera to the patient.

The computer is communicatively coupled to the x-ray detector to receive the x-ray images. The computer is communicatively, for example wired or wirelessly, coupled to the tracking device to receive the sensor data. The computer is configured to process the sensor data of the tracking device to generate tracking data. Processing of the sensor data by the computer comprises for example taking into account the rotation of the at least one marker during acquisition of the optical sensor data by the at least one camera when the at least one marker is arranged on a rotating component of the medical or dental imaging system. The computer is configured to calculate the three-dimensional x-ray image based on the plurality of x-ray images generated at different positions and received from the x-ray detector and on the tracking data to compensate for any movement of the head or head part to be imaged during the acquisition of the plurality of x-ray images. The computer may be physically linked to the frame or remote from the frame or any other part of the medical or dental imaging system. The computer comprises in particular software and/or algorithms to process the plurality of x-ray images generated at different positions, the sensor data and/or the tracking data and to calculate the three-dimensional x-ray image. The computer is preferably at least communicatively linked to a display or monitor to depict the calculated three-dimensional x-ray image.

The tracking device comprises the at least one camera and an attachment device for detachable attachment of the at least one camera to the patient, in particular to the head of a patient, such that the at least one camera faces and records at least one tracking marker of the tracking device in order to generate images of the at least one tracking marker.

By providing an attachment device which makes it possible to place the camera on the patient head, the visual effect of tilting the head or at least one head part to be imaged is magnified in an advantageous manner. If, e.g., the patient tilts the head with the camera positioned on the patient's head, the tilting motion results in a visible difference of the sensor data or a tracking marker image which is larger than images captured by known systems. In particular the sensor data and/or tracking data are magnified proportionally to the distance between the patient head and the at least one tracking marker, which is preferably located on a component of the medical or dental imaging system. As a result, a visibly magnified difference of the images of the markers is achieved and thus a more robust and accurate determination of particularly the tilting and nodding patient motion is achieved. Accordingly, the attachment of the camera on the head of a patient is particularly advantageous for medical or dental imaging systems having a chinrest, since, as described above, due to the chinrest the motions of the head are primarily constrained to be tilting or nodding motions which result in greater differences of the images of the markers.

The camera is preferably at least one of an optical camera taking pictures in the visible spectrum, a video camera or a digital camera. The camera preferably comprises a CCD sensor or a CMOS sensor. The sensor data generated or recorded by the camera preferably comprise optical or visible light sensor data.

The tracking device preferably comprises in addition at least one inertial sensor and an attachment device for detachable attachment of the at least one inertial sensor to the patient, in particular to the head of a patient or to the at least one part of the head, such that the at least one inertial sensor records any movement of the head or head part in order to generate sensor data.

The at least one inertial sensor provides in an advantageous manner a more reliable or robust motion detection in particular of large and abrupt motions of the head or head part to be imaged (e.g., of the oral region of the head). The provision of the at least one inertial sensor also extends the applicability of the medical or dental imaging system with respect to a broader range of patient motion, in particular since a patient motion can exceed the limited field of view of a camera.

The sensor data generated or recorded by the at least one inertial sensor preferably comprise inertial motion sensor data. The inertial motion sensor data may comprise for example at least one of acceleration data specifying a value of acceleration of the head part to be imaged or of the head or rotation data specifying the rotation or rotation velocity of the head part to be imaged or of the head.

The computer is communicatively, for example wired or wirelessly, coupled to the at least one inertial sensor to receive the inertial motion sensor data. The computer is configured to process the inertial motion sensor data of the tracking device to generate tracking data.

The at least one inertial sensor may comprise at least one of an accelerometer, a magnetometer or a gyroscope. The at least one inertial sensor preferably is one of a plurality of inertial sensors of the tracking device which, in particular, together form an inertial motion sensor unit. The inertial motion sensor unit may comprise only one sort of inertial sensor (e.g., only accelerometers or magnetometers or gyroscopes) or different types of said inertial sensors.

According to this especially preferred embodiment the tracking device comprises at least one camera, in particular as described above, and at least one inertial sensor, in particular as described above. The sensor data thus comprise optical sensor data provided by the at least one camera and inertial motion sensor data provided by the at least one inertial sensor. The computer is preferably configured to receive the optical and inertial motion sensor data and to process them to generate the tracking data, in particular combined tracking data comprising optical and inertial motion sensor data. The computer is preferably configured to calculate a three-dimensional x-ray image of the head or the at least one head part based on the plurality of x-ray images generated at different positions and on said optical and inertial, preferably combined tracking data to compensate for any movement of the head or head part to be imaged during the acquisition of the plurality of x-ray images.

The combination of at least one camera and at least one inertial sensor and the respective sensor and tracking data speed up in an advantageous manner the calculation or reconstruction of the three-dimensional x-ray image including the compensation for movements of the head or head part. The at least one inertial sensor preferably provides real time sensor or tracking data which in particular can be used as a starting point for the motion compensation or detection algorithm with positive effects on the total three-dimensional x-ray image calculation time, which is a key performance factor for medical or dental imaging devices.

In addition, as already described above, the inertial motion sensor data are used to make the tracking process and the tracking data more robust, in particular in case of large and abrupt patient motion. Preferably, the at least one inertial sensor and the respective inertial motion sensor data and/or the tracking data derived therefrom thus supplement the optical sensor data of the at least one camera and/or tracking data derived therefrom and in particular enable a more reliable motion detection and compensation of large and abrupt motions and thus extend the applicability of the medical or dental imaging system to a broader range of patient motion patterns.

The at least one camera and the attachment device are preferably movable relative to one another so that the at least one camera can be directed at the at least one tracking marker, in particular before the plurality of x-ray images of the at least one part of the head are taken. The at least one camera and the attachment device are preferably movable relative to one another such that the at least one camera can face and record the at least one tracking marker and/or that the at least one marker is in the field of view of the camera in order to generate images of the at least one tracking marker and/or optical sensor data. This provides in an advantageous manner for a more accurate recording of the at least one tracking marker through the at least one camera and/or to match the tracking device to patients having different body heights. In order to be movable relative to one another the at least one camera and the attachment device are preferably connected to one another in an articulated manner or by a hinge or a pivot joint or articulated joint.

The at least one camera and/or the at least one inertial sensor is/are preferably non-detachably attached to the attachment device which provides in an advantageous manner for a more secure connection.

The attachment device preferably comprises one of a strap or a belt. The attachment device preferably comprises a harness or a helmet-like headpiece. These embodiments provide in an advantageous manner for a comfortable fit for the patient and/or for a secure, tight fit of the at least one camera and/or the at least one inertial sensor. The attachment device may be made of at least one of a fabric, leather or plastic.

The attachment device is preferably adjustable to fit different patients, so that in advantageously one attachment device can be used for a plurality of people. The attachment device is, in particular, made of elastic material, for example an elastic fabric, or comprises an elastic portion, for example an elastic strap, to make it adjustable for different patients. Alternatively or in addition the attachment device preferably comprises an infinitely variable fastener portion, for example a Velcro fastener, or an incremental fastener, for example similar to a belt having a plurality of holes and a pin which can be selectively inserted into one of the holes.

The at least one camera and the at least one inertial sensor preferably comprise a shared or common attachment device, in particular, an attachment device as described above. A shared attachment device advantageously simplifies and shortens the arrangement of the at least one camera and the at least one inertial sensor on the patient (head). Especially preferably, the shared attachment device comprises a plurality of cameras, for example two or three cameras, and a single inertial sensor. This, embodiment provides for an especially fast, reliable and robust motion detection of the at least one head part to be imaged or head of the patient and thus for a reduced calculation time of the three-dimensional x-ray image by the computer.

The medical or dental imaging system preferably comprises at least one tracking marker that has a known positional relationship relative to at least one component of the medical or dental imaging system. Thus, the at least one tracking marker advantageously forms a reliable reference, in particular for the computer when calculating the three-dimensional x-ray image of the head or at least one head part and compensating for any movement of the head or head part.

The at least one tracking marker may be mounted for example on the rotation unit, in particular on the rotating arm of the rotation unit, on the x-ray source or the x-ray detector, or on a stationary or non-moving component of the medical or dental imaging system, for example on the frame or on a component that is connected to the frame. If a plurality of tracking markers is provided all of them can be arranged on the rotation unit or all of them can be arranged on a stationary component or at least one of them can be arranged on the rotation unit and at least one another can be arranged on a stationary component.

The at least one tracking marker of the medical or dental imaging system is preferably arranged on or fixed to the medical or dental imaging system. In particular, the at least one tracking marker is non-detachably arranged on the medical or dental imaging system, for example by an adhesive or mechanically. Thus, the at least one tracking marker advantageously forms a steady reference for the at least one camera. The at least one tracking marker may be mounted non-detachably for example on the rotation unit, in particular on the rotating arm of the rotation unit, on the x-ray source or the x-ray detector, or on a component that is attached to the frame.

The at least one tracking marker is preferably arranged, in particular centrically arranged, between the x-ray source and the x-ray detector. This in particular simplifies the recording of the at least one tracking marker by the at least one camera which is attached to the patient. The at least one tracking marker is especially preferably arranged on a portion of the rotation unit or rotating arm or on a stationary component of the medical or dental imaging system which is between the x-ray source and the x-ray detector, in particular close to or on the pivot point or pivot bearing which rotatably couples the rotation unit and the frame. Alternatively or in addition the at least one tracking marker is especially preferably arranged on a side of the rotation unit or rotating arm or stationary component which faces the chinrest or the head of the patient when resting on the chinrest, so that in an especially advantageous manner the at least one marker is continuously in the field of view of the at least one camera during the acquisition of x-ray images.

Alternatively or in addition the at least one tracking marker is preferably arranged on a part of the medical or dental imaging system which is located above the patient, in particular above the head of the patient, when the patient takes a position in which the rotation unit moves around the head or head part to be imaged and the x-ray source and the x-ray detector take up a plurality of different positions to generate a plurality of x-ray images at said different positions. This configuration advantageously establishes a direct optical connection between the at least one camera and the at least one tracking marker when the at least one camera is arranged on the head of the patient, and thus provides optimal conditions for the recording of the at least one tracking marker by the at least one camera. In particular, the at least one tracking marker is arranged on a stationary or rotatable part of the medical or dental imaging system which is located above the patient in order to advantageously form a reference of the tracking device which is continuously in the field of view of the at least one camera during the acquisition of the x-ray images. For example, the at least one tracking marker is arranged either on a non-rotating part of the frame or on a component of the medical or dental imaging system which is movably connected to the frame and which is preferably close to or on the pivot point or next to the pivot bearing which rotatably couples the rotation unit and the fixed arm of the frame.

The at least one tracking marker preferably comprises an optical marker which can be recognized by the at least one camera. The optical marker comprises for example at least one of a color marker, a marker having a predetermined geometrical shape or a marker having a predetermined geometrical circumference. The tracking device preferably comprises a plurality of tracking markers, wherein at least two of the plurality of tracking markers differ in their appearance, for example they have different colors and/or different shapes, which advantageously further supports the motion detection of the tracking device.

The medical or dental imaging system preferably comprises a wireless or wired communication link between the computer and the at least one camera for transmission of the images of the at least one tracking marker and between the computer and the at least one inertial sensor for transmission of the inertial motion sensor data. A wireless communication link advantageously provides for a data communication which is easy to handle, in particular with respect to the rotation unit. The wireless communication link preferably comprises a short-range communication, for example through radio frequencies, Bluetooth, Wi-fi, etc.

A wired communication link advantageously provides for a secure transmission of data which is less susceptible to external interference. The wired communication link advantageously comprises at least one connection wire which communicatively and physically connects the at least one camera and/or the at least one inertial sensor and/or the at least one attachment device and the computer and which is configured to transmit the sensor data to the computer. Especially preferable, a single or shared connection wire is provided which communicatively connects to any camera and inertial sensor of an attachment device and is configured to transmit the optical and inertial motion sensor data of all cameras and inertial sensors to the computer.

The wireless communication link preferably comprises a wireless transmitter communicatively coupled to the at least one camera and/or the at least one inertial sensor and configured to wirelessly transmit the optical or optical and inertial motion sensor data and a wireless receiver communicatively coupled to the computer and configured to receive the wirelessly transmitted sensor data and to pass them on to the computer. The wireless transmitter can be integral with the at least one camera or the at least one inertial sensor or remote or separated from it/them. Due to the limited space on the attachment device an integral, one-piece unit having the at least one camera or the at least one inertial sensor and the wireless transmitter is advantageous. The wireless receiver can be integral with the computer or remote or separated from the computer.

If the tracking device comprises a plurality of cameras the wireless communication link preferably comprises a shared or common wireless transmitter for at least two of the plurality of cameras to wirelessly transmit the optical sensor data. If the tracking device comprises a plurality of inertial sensors the wireless communication link preferably comprises a shared or common wireless transmitter for at least two of the plurality of inertial sensors to wirelessly transmit the inertial motion sensor data. If the tracking device comprises at least one camera and at least one inertial sensor the wireless communication link preferably comprises a shared or common wireless transmitter for the at least one camera and the at least one inertial sensor to wirelessly transmit the optical and inertial motion sensor data. These embodiments advantageously provide a simpler and cheaper tracking device, since only a single or a small number of wireless transmitter(s) is used. In each of these embodiments the shared wireless transmitter can be integral with one of the camera(s) or of the inertial sensor(s), which may be advantageous due to the limited space on the attachment device, or remote or separated from any camera(s) or inertial sensor(s). Alternatively, if there is more than one camera and/or inertial sensor each of these cameras and/or inertial sensors can have its own wireless transmitter.

The wireless transmitter is preferably configured to be detachably attached to the patient, in particular to the head of a patient, by an attachment device. The attachment device preferably comprises an attachment device as described above. Especially preferred the wireless transmitter, in particular the shared integral or remote wireless transmitter, and the at least one camera and/or the at least one inertial sensor have a shared attachment device, in particular one as described above. This advantageously simplifies the handling of the at least one camera and/or the at least one inertial sensor and the wireless transmitter.

According to an embodiment an attachment device for a medical or dental imaging system configured to generate an image of at least one part of the head of a patient, comprises attachment means, in particular at least one attachment element, for detachable attachment of the attachment device to a patient, in particular to the head of the patient, at least one camera configured to generate images of at least one tracking marker and at least one inertial sensor configured to generate inertial motion sensor data, wherein the images of the at least one tracking marker and the inertial motion sensor data are provided for compensation for any movement of the at least one part of the head during the acquisition of the image of the at least one part of the head.

The attachment device preferably comprises at least one or more of the characteristics and/or components of the attachment devices described above, for example a connection wire for a wired communication link to the computer or a wireless transmitter, so that to avoid repetition reference is made to the above description and embodiments.

These and other embodiments will be described below with reference to the following drawings.

DETAILED DESCRIPTION

Figure 1:
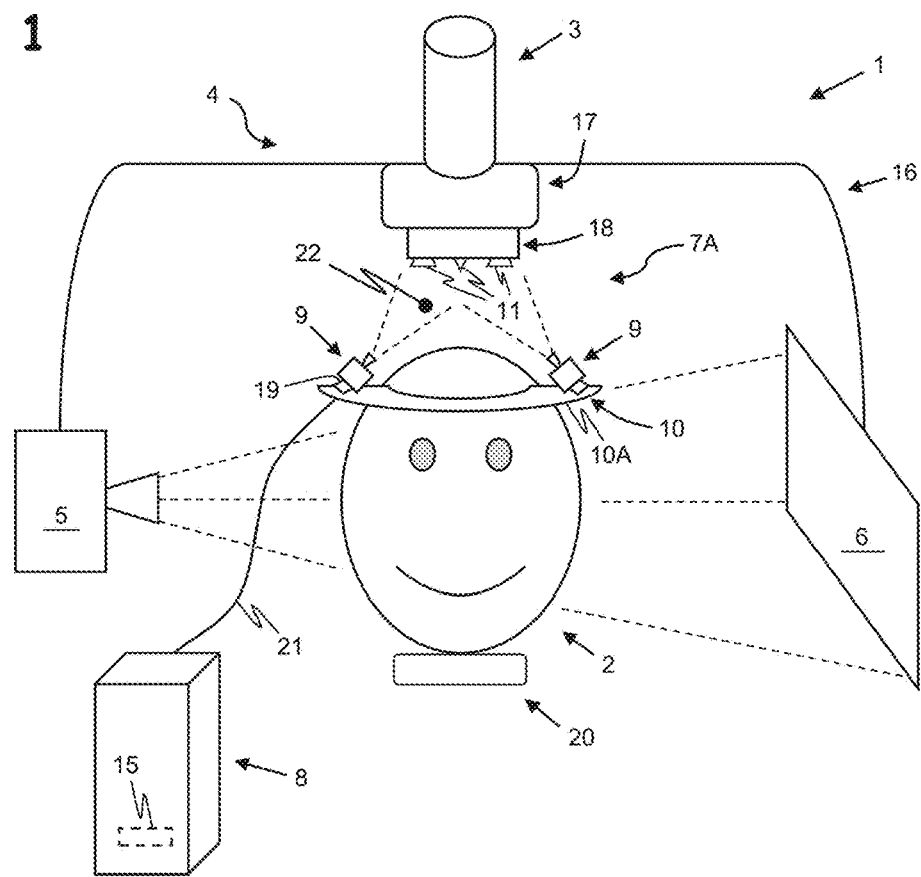
FIG. 1 schematically shows a first embodiment of a medical or dental imaging system for generating an image of at least a part of the head of a patient with a tracking device having a plurality of cameras and a wired communication link.

Each medical or dental imaging system 1 for generating an image of at least one part of the head 2 of a patient shown in FIGS. 1-4 comprises a frame or supporting structure 3 (only an end portion of the frame is depicted), a rotation unit 4 rotatably coupled to the frame 3, a tracking device 7A-7D which is configured to provide sensor data indicative of any movement of the at least one part of the head 2 to be imaged, a chinrest 20 and a computer 8 (not shown in FIG. 4, but can also be implemented there) configured to calculate a three-dimensional x-ray image of at least a part the head 2.

Rotation unit 4 comprises an x-ray source 5 for the emission of x-rays towards the head 2 or the at least one part of the head 2 to be imaged and an x-ray detector 6 which is configured to receive at least a portion of the x-rays emitted by the x-ray source 5, in particular the x-rays which have penetrated the head 2 or head part to be imaged. The rotation unit 4 comprises a cantilever or a rotating arm 16 having two opposing end sections, wherein the x-ray source 5 is attached to one of these respective end sections and the x-ray detector 6 is attached to the other of these respective end sections.

Rotation unit 4, in particular rotating arm 16 is rotatably coupled to the frame 3 by a pivot bearing 17 so that the rotation unit 4 with the x-ray source 5 and the x-ray detector 6 is configured to rotate around the head 2 or head part to be imaged. Accordingly, the x-ray source 5 and the x-ray detector 6 can take up a plurality of different positions relative to head 2 or head part to generate a plurality of x-ray images of the at least one part of head 2 at said different positions. A cover or cap 18 may be provided to cover the pivot bearing 17 or the pivot point, see FIGS. 1, 3, 4. Cap 18 can either be a part of the rotation unit 4 and in particular rotate together with the rotation unit 4 or alternatively be a stationary part of the medical or dental imaging system 1 which in particular is coupled to the frame 3.

Computer 8 is configured to process the sensor data received from the tracking device 7A-7D to generate tracking data and to calculate a three-dimensional x-ray image of the at least one part of head 2 based on the plurality of x-ray images of the head 2 or the at least one part of head 2 generated by the x-ray detector 6 at different positions and on the tracking data to compensate for any movement of the head 2 or head part during the acquisition of the plurality of x-ray images. Thus, the computer 8 is communicatively coupled to the x-ray detector 6 and to the tracking device 7A-7D via a wired communication link 21 (see FIGS. 1 and 3) or a wireless communication link 13 (see FIGS. 2 and 4) for transmission of the sensor data.

The wireless communication link 13 preferably uses Bluetooth or a similar technology. The computer 8 comprises a wireless receiver 15, preferably integrally arranged within a housing of the computer 8, configured to wirelessly communicate with the tracking device 7A-7D to receive the sensor data. The wireless receiver 15 is preferably configured to wirelessly communicate with the x-ray detector 6 to receive the x-ray images of the head 2 or at least one head part.

The wired communication link 21 advantageously comprises at least one connection wire which communicatively and physically connects the tracking device 7A-7D and the computer 8 and which is configured to transmit the sensor data to the computer 8.

Computer 8 comprises a processor or microcontroller, in particular with software and/or algorithms, for processing the x-ray images of the head 2 or at least one head part and the sensor data received from the tracking device 7A-7D to generate the tracking data and for calculation or reconstruction of the three-dimensional x-ray image and compensation for any movement of the head 2 or at least one head part during the recording of the x-ray images.

Tracking device 7A-7D is configured to provide sensor data indicative of any movement of the at least one part of the head 2 during the acquisition of the plurality of x-ray images of the at least one part of the head 2 and to communicatively transmit the sensor data to computer 8. Each tracking device 7A-7D comprises an attachment device 10 having attachment means or at least one attachment element 10A for detachable attachment to the patient, in particular to the head 2 or head part to be imaged. The attachment device 10 is configured to be fastened to the head 2, preferably before the plurality of x-ray images are taken, and to be removed from the head 2, preferably after the plurality of x-ray images are taken. The attachment device 10 is preferably configured to be attached to the top of the head 2. The attachment means or attachment element 10A may comprise for example a belt or strap.

The differences between the various tracking devices 7A-7D according to the embodiments of FIGS. 1-4 are discussed below.

Figure 2:
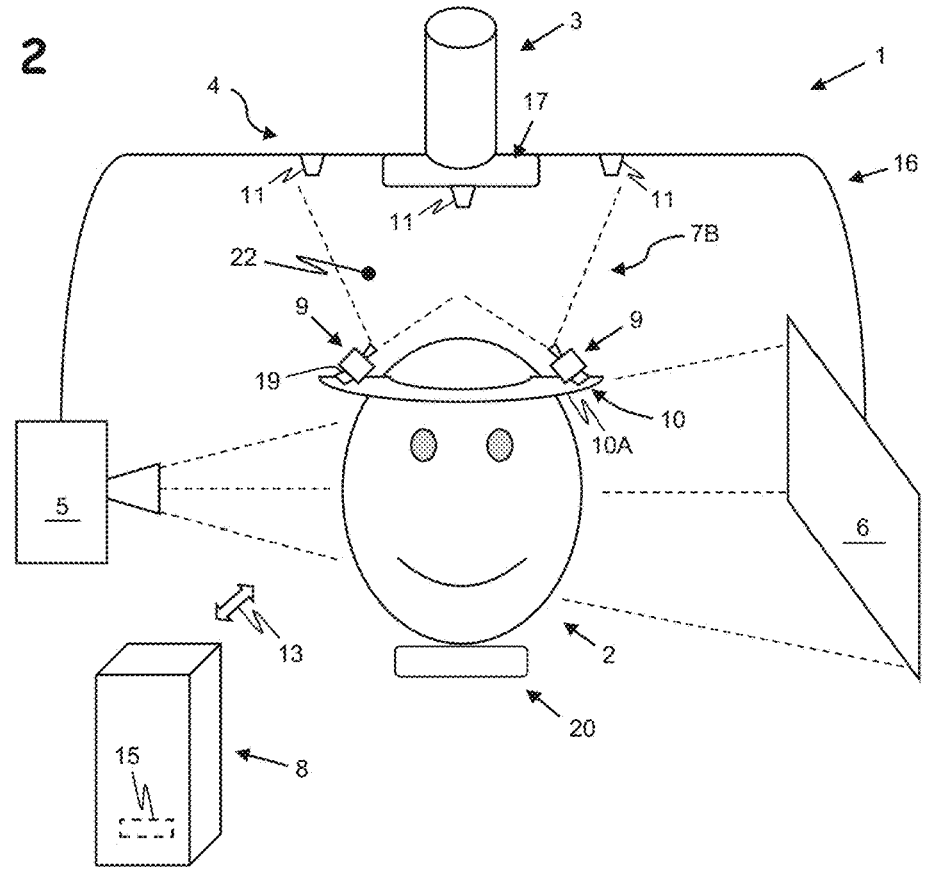
FIG. 2 schematically shows a second embodiment of a medical or dental imaging system for generating an image of at least a part of the head of a patient with a tracking device having a plurality of cameras and a wireless communication link.

Tracking devices 7A and 7B of FIGS. 1 and 2 comprise a plurality, for example two cameras 9 which are arranged or mounted on the attachment device 10, 10A, so that the two cameras 9 together with attachment device 10, 10A can be or are detachably attached to the patient's head 2. Tracking device 7A further comprises a plurality, for example three, tracking markers 11 which have a known positional relationship relative to at least one component of the medical or dental imaging system 1. In order to have this known positional relationship the tracking markers 11 are arranged on the medical or dental imaging system 1 between the x-ray source 5 and the x-ray detector 6.

All tracking markers 11 of tracking device 7A of FIG. 1 are arranged stationary or non-movably relative to the rotation unit 4. The tracking markers 11 are in particular disposed adjacent to the rotating pivot bearing 17 on cover 18 which covers pivot bearing 17 and which is immovably or stationary coupled to a stationary part of the frame 3.

Referring to tracking device 7B of FIG. 2 at least one or more of the tracking markers 11 is/are arranged on the rotating arm 16 of rotation unit 4. At least one tracking marker is arranged on or adjacent to pivot bearing 17.

In each of the embodiments of FIGS. 1 and 2, the markers are disposed on the medical or dental imaging device 1, such that at least one of the markers 11 is always visible by at least one camera 9 at any time during acquisition of the x-ray images. As can be seen in FIGS. 1 and 2 the tracking markers 11 are disposed above the patient or the head 2 and thus above attachment device 10, 10A and cameras 9 when the patient takes a position between the x-ray source 5 and the x-ray detector 6, so that the rotation unit 4 can move or moves around the head 2 or head part to be imaged to generate a plurality of x-ray images at different positions. In particular the tracking markers 11 are disposed on stationary cover 18 or on rotating arm 16, such that they face at least one of the head 2 or part of the head to be imaged or the chinrest.

The dashed lines schematically show the field of view 22 of the cameras 9. As can be seen in FIGS. 1 and 2, the provision of the tracking markers 11 between the x-ray source 5 and the x-ray detector 6, in particular on the stationary cover 18 or the rotating pivot bearing 17 and/or rotating arm 16, guarantees that the tracking markers 11 are always in the field of view 22, even when the rotation unit 4 rotates and that thus the tracking markers 11 are never hidden by the rotation unit 4 or a component of the rotation unit 4.

In the embodiment depicted in FIG. 2, due to the arrangement of the tracking markers 11 on the rotation unit 4 or any component rotating with the rotation unit 4 the tracking markers 11 are set into rotation when the rotation unit 4 rotates, in particular when the x-ray images are generated. Accordingly, the optical sensor data of the cameras 9 show the rotation of the tracking markers 11. The computer 8, in particular software and/or algorithms of computer 8, is configured to take into account or eliminate the rotation of the tracking markers 11 when generating the tracking data.

The cameras 9 of the FIGS. 1 and 2 are configured to record images of the tracking markers 11 and/or to generate optical sensor data. The cameras 9, in particular image capturing components of the cameras 9, like a lens, an objective or an aperture, can be or are arranged such on the patient and/or on the attachment device 10, 10A that they face the tracking markers 11 and thus can record the tracking markers 11 in order to generate images of the tracking markers 11 and/or sensor data. At least one or more of the cameras 9 and the attachment device 10 are movably coupled to one another so that the cameras 9, in particular image capturing components of the cameras 9, can be aimed at the tracking markers 11 to generate images of the tracking markers 11 and/or that each of the tracking markers 11 is at least in one field of view 22 of one of the cameras 9. In order to be movable relative to one another the camera(s) 9 and at least one element 10A of the attachment device 10 are connected to one another in an articulating manner, for example by a hinge or an articulated joint 19.

The images of the tracking markers 11 and/or sensor data show or log the movements of the head 2 or the at least one head part to be imaged. These images of the tracking markers 11 and/or sensor data are then communicated to computer 8. According to FIG. 1 this is achieved by a wired communication link 21 as described above.

According to FIG. 2 the sensor data are communicated to computer 8 by a wireless communication link 13 as described above. The wireless communication link 13 comprises at least one wireless transmitter which is configured to wirelessly transmit the images of the tracking markers 11 and/or optical sensor data of the cameras 9 to wireless receiver 15 of computer 8. According to this embodiment the wireless transmitter is arranged inside or integrally with one of the cameras 9 and is thus not shown.

According to FIGS. 1 and 2 computer 8 uses these transmitted images and/or sensor data of tracking device 7A or 7B to compensate for any movement of the head 2 or head part to be imaged during the acquisition of the plurality of x-ray images by x-ray detector 6 when calculating the three-dimensional x-ray image.

Figure 3:
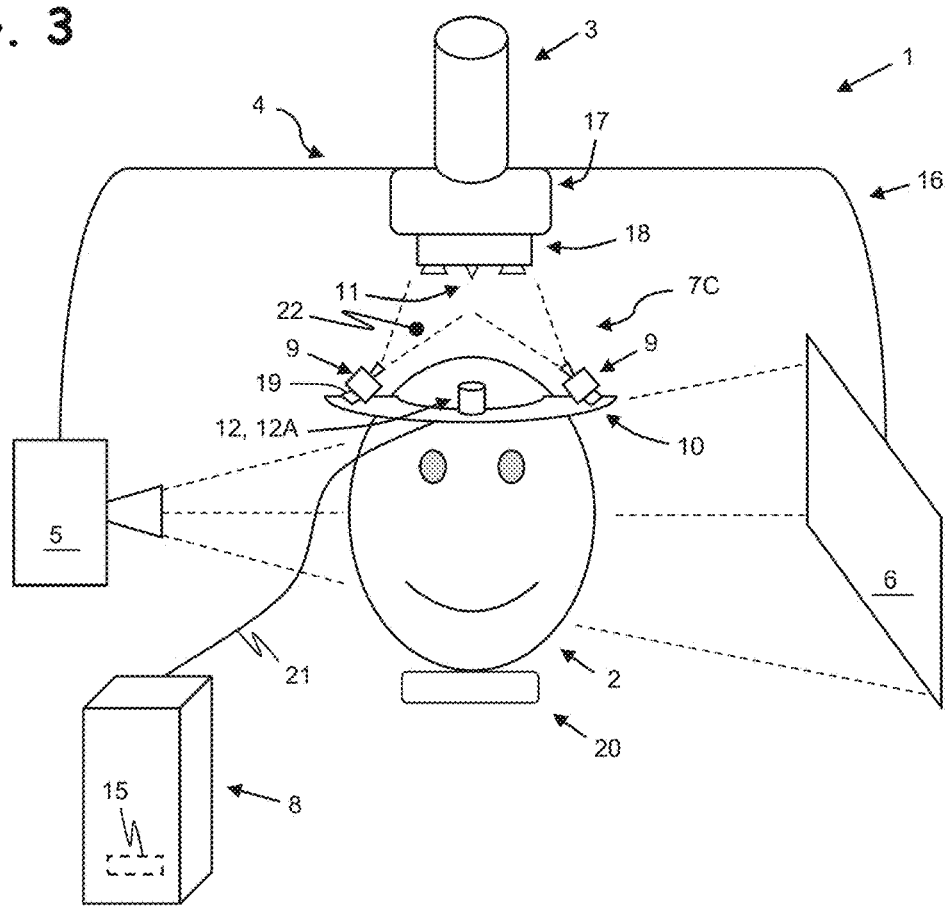
FIG. 3 schematically shows a third embodiment of a medical or dental imaging system for generating an image of at least a part of the head of a patient with a tracking device having a plurality of cameras and an inertial sensor and a wired communication link.

Tracking device 7C of FIG. 3 comprises two cameras 9 and additionally at least one inertial sensor 12A, preferably a plurality of inertial sensors 12A which are packed together in an inertial motion sensor unit 12. The inertial sensor 12A or unit 12 is configured to record any movement of the head 2 or the at least one head part in order to generate inertial motion sensor data.

The two cameras 9 and inertial sensor 12A or unit 12 are arranged or mounted on a shared attachment device 10, 10A, so that the cameras 9 and inertial sensor 12A or unit 12 together with attachment device 10, 10A can be or are detachably attached to the patient's head. The two cameras 9 correspond to the cameras 9 of FIGS. 1 and 2, so that to avoid repetition reference is made to the description of these Figures.

Corresponding to FIGS. 1 and 2 the images of the tracking markers 11 and/or optical sensor data of the cameras 9 and in addition the inertial motion sensor data show or log the movements of the patient, in particular of the head or head part to be imaged. The optical and inertial motion sensor data are communicated to computer 8 by the wired communication link 21 as described above. Computer 8 uses both, the images of the tracking markers 11 recorded by the cameras 9 and the inertial motion sensor data to compensate for any movement of the head 2 or head part during the acquisition of the plurality of x-ray images by x-ray detector 6 when calculating the three-dimensional x-ray image.

Figure 4:
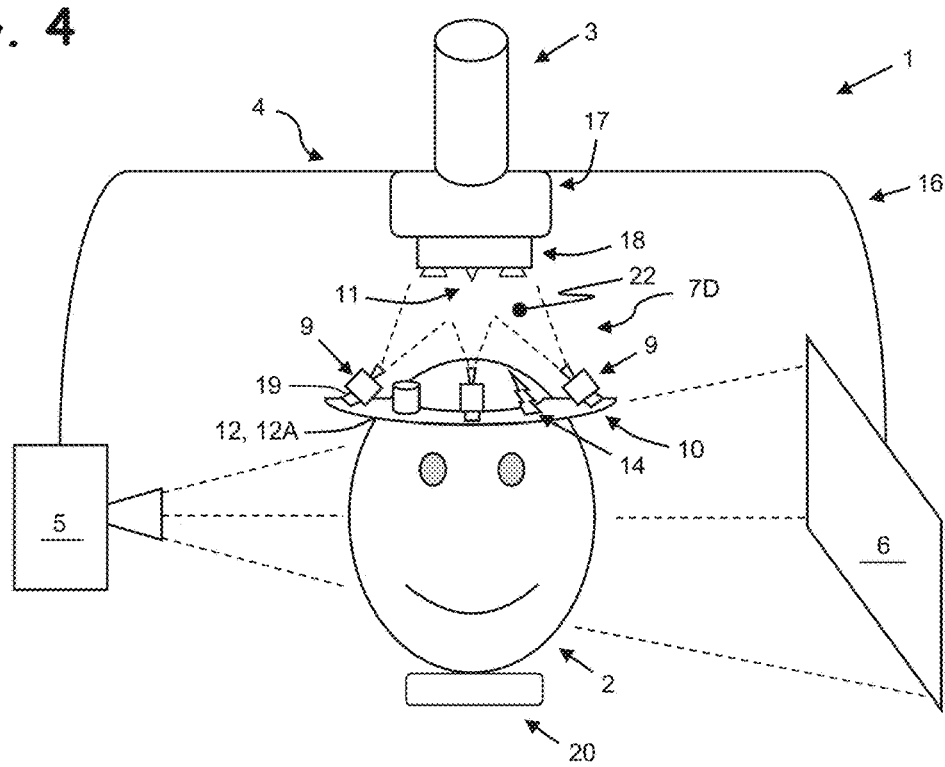
FIG. 4 schematically shows a fourth embodiment of a medical or dental imaging system for generating an image of at least a part of the head of a patient with a tracking device having a plurality of cameras, an inertial sensor and a separate wireless transmitter.

Tracking device 7D of FIG. 4 comprises a separate or remote wireless transmitter 14, three cameras 9 and at least one inertial sensor 12A or an inertial motion sensor unit 12. Separate or remote wireless transmitter 14 is not integrated into one of the cameras 9 or the inertial sensor 12A but is a discrete or self-contained device. The cameras 9, inertial sensor 12A or unit 12 and wireless transmitter 14 are arranged or mounted on a shared attachment device 10, 10A, so that these devices 9, 12A, 12 and 14 together with attachment device 10, 10A can be or are detachably attached to the patient's head. The three cameras 9 correspond to the cameras 9 of FIGS. 1, 2 and 3 and inertial sensor 12A or unit 12 corresponds to the sensor 12A or unit 12 of FIG. 3, so that to avoid repetition reference is made to the description of these Figures.

Corresponding to FIGS. 1, 2 and 3 the images of the tracking markers 11 and/or optical sensor data of the cameras 9 and the inertial motion sensor data show or log the movements of the patient, in particular of the head 2 or head part to be imaged. Separate wireless transmitter 14 is communicatively linked to each of cameras 9 and to the at least one inertial sensor 12A and configured to receive their images and sensor data and to wirelessly transmit them to wireless receiver 15 of computer 8 (see FIG. 2). Computer 8 uses both, the images of the tracking markers 11 and/or optical sensor data of the cameras 9 and the inertial motion sensor data to compensate for any movement of the head 2 or head part during the acquisition of the plurality of x-ray images by x-ray detector 6 when calculating the three-dimensional x-ray image.

All tracking markers 11 of tracking devices 7C and 7D shown in FIGS. 3 and 4 are arranged stationary or non-movably relative to the rotation unit 4 as depicted and discussed with reference to FIG. 1. The tracking markers 11 are in particular disposed adjacent to the rotating pivot bearing 17 on cover 18 which covers pivot bearing 17 and which is immovably or stationary coupled to a stationary part of the frame 3. Alternatively, at least one or more or all of the tracking markers 11 of tracking devices 7C and 7D shown in FIGS. 3 and 4 can be arranged on the rotation unit 4, in particular on rotating arm 16 as depicted and discussed with reference to FIG. 2.

The embodiments described or shown, in particular, serve to depict the invention. The characteristics, disclosed in an embodiment, are therefore not limited to that embodiment, but can rather be combined individually or together with one or more characteristics of one of the other embodiments.

What is claimed is:

1. A medical or dental imaging system for generating an image of at least one part of a head of a patient, comprising:
    a frame,
    a rotation unit having an x-ray source for the emission of x-rays towards the head of the patient and an x-ray detector which is configured to receive at least a portion of the x-rays emitted by the x-ray source, wherein the rotation unit is coupled to the frame and is configured to move around the head so that the x-ray source and the x-ray detector take up a plurality of different positions to generate a plurality of x-ray images of the at least one part of the head at said different positions,
    a tracking device which is configured to provide sensor data indicative of any movement of the at least one part of the head during the acquisition of the plurality of x-ray images of the at least one part of the head, wherein the tracking device comprises a plurality of cameras and a plurality of tracking markers, wherein the plurality of cameras and the plurality of tracking markers are spatially separated such that all cameras of the plurality of cameras are attached to the patient and all tracking markers of the plurality of tracking markers are arranged on the medical or dental imaging system, and
    a computer communicatively coupled to the x-ray detector and to the tracking device and configured to receive and process the sensor data of the tracking device to generate tracking data and to calculate a three-dimensional x-ray image of the at least one part of the head based on the plurality of x-ray images generated at different positions and on the tracking data to compensate for any movement of said at least one part of the head during the acquisition of the plurality of x-ray images, wherein
    the plurality of cameras comprises an attachment device for detachable attachment of the plurality of cameras to the patient such that the plurality of cameras faces and records the plurality of tracking markers of the tracking device in order to generate the sensor data comprising images of the plurality of tracking markers.

2. The medical or dental imaging system according to claim 1, wherein
    the tracking device further comprises at least one inertial sensor and an attachment device for detachable attachment of the at least one inertial sensor to the patient such that the at least one inertial sensor records any movement of the at least one part of the head in order to generate the sensor data comprising inertial motion sensor data.

3. The medical or dental imaging system according to claim 2, wherein
    the plurality of cameras and the at least one inertial sensor comprise a shared attachment device, wherein the plurality of cameras and the shared attachment device are movable relative to one another without moving the at least one inertial sensor.

4. The medical or dental imaging system according to claim 2, comprising
    a wired or wireless communication link between the computer and the at least one inertial sensor for wireless transmission of the sensor data.

5. The medical or dental imaging system according to claim 2, wherein
    the at least one inertial sensor comprises at least one of an accelerometer, a magnetometer or a gyroscope.

6. The medical or dental imaging system according to claim 1, wherein
    the plurality of cameras and the attachment device are movable relative to one another so that the plurality of cameras can be directed at the plurality of tracking markers.

7. The medical or dental imaging system according to claim 1, wherein
    the attachment device comprises at ne of a strap or a belt.

8. The medical or dental imaging system according to claim 1, wherein
    the attachment device is adjustable to fit different patients.

9. The medical or dental imaging system according to claim 1, wherein
    the plurality of tracking markers has a known positional relationship relative to at least one component of the medical or dental imaging system.

10. The medical or dental imaging system according to claim 9, wherein
    at least one tracking marker of the plurality of tracking markers is arranged non-movably relative to the rotation unit.

11. The medical or dental imaging system according to claim 9, wherein
    at least one tracking marker of the plurality of tracking markers is arranged between the x-ray source and the x-ray detector.

12. The medical or dental imaging system according to claim 9, wherein
    at least one tracking marker of the plurality of tracking markers is arranged on a part of the rotation unit of the medical or dental imaging system.

13. The medical or dental imaging system according to claim 9, wherein
    at least one tracking marker of the plurality of tracking markers is located such that the at least one tracking marker is in a field of view of the at least one camera of the plurality of cameras when the patient wearing the attachment device with the plurality of cameras occupies a position in which the rotation unit moves around the head and the x-ray source and the x-ray detector occupy a plurality of different positions to generate a plurality of x-ray images at said different positions.

14. The medical or den a imaging system according to claim 1, comprising
    a wired communication link between the computer and the at least one camera for transmission of the sensor data.

15. The medical or dental imaging system according to claim 1, comprising
    a wireless communication link between the computer and the plurality of cameras transmission of the sensor data.

16. The medical or dental imaging system according to claim 15, wherein
    the wireless communication link comprises a wireless transmitter communicatively coupled to the plurality of cameras and configured to wirelessly transmit the sensor data, and a wireless receiver communicatively coupled to the computer and configured to receive the wirelessly transmitted sensor data and to transmit received sensor data to the computer.

17. The medical or dental imaging system according to claim 16, wherein
    the wireless transmitter is configured to be detachably attached to the patient by an attachment device.

18. A medical or dental imaging system for generating an image of at least one part of a head of a patient, comprising:
- a frame,
- a rotation unit having an x-ray source for the emission of x-rays towards the head of the patient and an x-ray detector which is configured to receive at least a portion of the x-rays emitted by the x-ray source, wherein the rotation unit is coupled to the frame and is configured to move around the head so that the x-ray source and the x-ray detector take up a plurality of different positions to generate a plurality of x-ray images of the at least one part of the head at said different positions,
- a tracking device which is configured to provide sensor data indicative of any movement of the at least one part of the head during the acquisition of the plurality of x-ray images of the at least one part of the head,
- a computer communicatively coupled to the x-ray detector and to the tracking device and configured to receive and process the sensor data of the tracking device to generate tracking data and to calculate a three-dimensional x-ray image of the at least one parr of the head based on the plurality of x-ray images generated at different positions and on the tracking data to compensate for any movement of said at least one part of the head during the acquisition of the plurality of x-ray images, wherein
- the tracking device comprises at least one camera and an attachment device for detachable attachment of the at least one camera to the patient such that the at least one camera faces and records at least one tracking marker of the tracking device in order to generate the sensor data comprising images of the at least one tracking marker, and
- at least one tracking marker that has a known positional relationship relative to at least one component of the medical or dental imaging system, wherein
- the at least one tracking marker is arranged on a stationary part of the frame of the medical or dental imaging system.

19. The medical or dental imaging system according to claim 18, wherein
- the at least one tracking marker is located such that the at least one tracking marker is in a field of view of the at least one camera when the patient wearing the attachment device with the at least one camera occupies a position in which the rotation unit moves around the head and the x-ray source and the x-ray detector occupy a plurality of different positions to generate a plurality of x-ray images at said different positions.

20. The medical or dental imaging system according to claim 18, wherein
- the tracking device further comprises an inertial sensor arranged on the attachment device and configured to generate inertial motion sensor data, wherein
- the sensor data comprising images of the at least one tracking marker provided by the at least one camera and the inertial motion sensor data are provided for compensation for any movement of the at least one part of the head of which the plurality of x-ray images is generated during the acquisition of the image of the at least one part of the head.

* * * * *

UNITED STATES PATENT AND TRADEMARK OFFICE
CERTIFICATE OF CORRECTION

PATENT NO. : 11,701,070 B2
APPLICATION NO. : 17/242949
DATED : July 18, 2023
INVENTOR(S) : Landi et al.

It is certified that error appears in the above-identified patent and that said Letters Patent is hereby corrected as shown below:

In the Claims

Column 14, Line 9, Claim 7 "at new of a strap" should read --at least one of a strap--.

Column 14, Line 44, Claim 13 "medical or den a imaging" should read --medical or dental imaging--.

Column 15, Line 21, Claim 18 "one parr of the head" should read --one part of the head--.

Signed and Sealed this
Tenth Day of October, 2023

Katherine Kelly Vidal
*Director of the United States Patent and Trademark Office*